(12) United States Patent
Bloemer et al.

(10) Patent No.: US 7,670,378 B2
(45) Date of Patent: Mar. 2, 2010

(54) IMPLANT FOR INSERTION INTO A BONE CAVITY OR BETWEEN VERTEBRAL BODIES

(75) Inventors: Wilhelm Bloemer, Unteruhldingen-Muehlhofen (DE); Jens Beger, Tuttlingen (DE); Ulrich Fink, Tuttlingen (DE); Cécile Wagner, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 760 days.

(21) Appl. No.: 11/156,243

(22) Filed: Jun. 17, 2005

(65) Prior Publication Data
US 2006/0009844 A1 Jan. 12, 2006

(30) Foreign Application Priority Data
Jun. 18, 2004 (DE) .................. 10 2004 030 347

(51) Int. Cl.
*A61F 2/44* (2006.01)
(52) U.S. Cl. ............... 623/17.16; 623/17.11; 623/17.12
(58) Field of Classification Search ... 623/17.11–17.16, 623/7–8
See application file for complete search history.

(56) References Cited

U.S. PATENT DOCUMENTS

| | | | |
|---|---|---|---|
| 5,047,055 A | | 9/1991 | Bao et al. |
| 5,176,692 A | | 1/1993 | Wilk et al. |
| 5,192,326 A | * | 3/1993 | Bao et al. ................. 623/17.12 |
| 5,500,013 A | * | 3/1996 | Buscemi et al. ............ 623/1.22 |
| 5,549,679 A | | 8/1996 | Kuslich |
| 5,571,189 A | | 11/1996 | Kuslich |
| 5,976,187 A | * | 11/1999 | Richelsoph ............... 623/17.16 |
| 6,005,020 A | * | 12/1999 | Loomis ....................... 523/105 |
| 6,099,565 A | * | 8/2000 | Sakura, Jr. ..................... 623/8 |
| 6,214,045 B1 | * | 4/2001 | Corbitt et al. .................. 623/8 |

(Continued)

FOREIGN PATENT DOCUMENTS

DE 39 22 203 10/1990

(Continued)

OTHER PUBLICATIONS

Wu et al., Preparation of collagen-based materials for wound dressing, Chinese Medical Journal, 2003, 116(3), pp. 419-423.*

(Continued)

*Primary Examiner*—Eduardo C Robert
*Assistant Examiner*—Julianna N Harvey
(74) *Attorney, Agent, or Firm*—Lipsitz & McAllister LLC

(57) ABSTRACT

The invention is related to an implant, in particular a bone replacement implant for insertion into a bone cavity, or an intervertebral implant for insertion between two adjacent vertebral bodies of a human or animal spine. The implant can be brought from a normal position, in which the implant encompasses a maximum total volume, into an insertion position, in which the implant encompasses an insertion volume, which is smaller than the maximum total volume. Moreover, the implant has a plurality of cavities in fluidic connection with one another, and a net volume encompassed in the normal position by the plurality of cavities in fluidic connection with one another is smaller than the maximum total volume, which allows insertion of the implant through as small as possible an opening in a human or animal body while maintaining a high inherent stability.

18 Claims, 3 Drawing Sheets

U.S. PATENT DOCUMENTS

| | | |
|---|---|---|
| 6,224,630 B1 | 5/2001 | Bao et al. |
| 6,280,475 B1 | 8/2001 | Bao et al. |
| 6,409,765 B1 * | 6/2002 | Bianchi et al. ............ 623/17.11 |
| 6,582,466 B1 * | 6/2003 | Gauchet .................. 623/17.11 |
| 6,811,570 B1 * | 11/2004 | Gehl ........................ 623/23.75 |
| 2002/0107437 A1 * | 8/2002 | Sirimanne et al. ........... 600/407 |
| 2004/0110285 A1 * | 6/2004 | Lendlein et al. ............. 435/366 |

FOREIGN PATENT DOCUMENTS

| | | |
|---|---|---|
| DE | 39 43 485 | 11/1990 |
| DE | 691 12 425 | 2/1996 |
| DE | 198 11 264 | 9/1999 |
| DE | 19858579 A1 * | 6/2000 |
| DE | 691 32 149 | 11/2000 |
| DE | 100 09 464 | 9/2001 |
| DE | 100 24 922 | 1/2002 |
| DE | 695 22 060 | 5/2002 |
| DE | 699 17 267 | 9/2004 |
| DE | 695 32 528 | 1/2005 |
| WO | 95/31948 | 11/1995 |
| WO | 02/43628 | 6/2002 |
| WO | 03/007853 | 1/2003 |

OTHER PUBLICATIONS

Lendlein et al., Shape-Memory Polymers, Angew. Chem. Int. Ed. 2002, 41, 2034-2057.*

* cited by examiner

IMPLANT FOR INSERTION INTO A BONE CAVITY OR BETWEEN VERTEBRAL BODIES

The present disclosure relates to the subject matter disclosed in German application number 10 2004 030 347.9 of Jun. 18, 2004, which is incorporated herein by reference in its entirety and for all purposes.

BACKGROUND OF THE INVENTION

The present invention relates to an implant, in particular a bone replacement implant for insertion into a bone cavity formed by resection, for example, or an intervertebral implant for insertion between two adjacent vertebral bodies of a human or animal spine, which can be brought from a normal position, in which the implant encompasses a maximum total volume, into an insertion position, in which the implant encompasses an insertion volume, which is smaller than the maximum total volume.

For treatment of a disc prolapse, the affected intervertebral disc is usually partially or completely removed and the section of the spine formed by the two vertebrae adjacent to the damaged disc reinforced. To achieve such a reinforcement, the two vertebral bodies of the adjacent vertebrae are usually fused by means of a spacer, also referred to as a "cage". The spacer is inserted between the two vertebral bodies, wherein a spacer is usually selected that has a height corresponding to the original height of the intervertebral disc. The spacer is preferably not solid, so that bone substance can grow into the spacer.

The disadvantage with such implants has proved to be their size, i.e. they cannot typically be inserted in a minimally invasive manner.

In addition, inserted balloons are known in particular in vertebroplasty, which are inserted into a bone cavity and can be filled with bone cement. The disadvantage with such implants is that they are not at all suitable as intervertebral implants, since such a balloon implant always expands in the direction of least resistance, particularly upon filling with a fluid.

Therefore, it is an object of the present invention to improve an implant of the above-described type such that the implant can be inserted through as small as possible an opening in a human or animal body and nevertheless have a high inherent stability.

SUMMARY OF THE INVENTION

This object is achieved according to the invention with an implant of the aforementioned type in that the implant has a plurality of cavities in fluidic connection with one another, and that a net volume encompassed in the normal position by the plurality of cavities in fluidic connection with one another is smaller than the maximum total volume.

As a result of the configuration of the plurality of cavities in fluidic connection with one another, the implant has a frame-like structure, which assures optimum dimensional stability. No overall deformation of the implant such as in the case of the known balloons results particularly when filling the cavities in fluidic connection with one another with a fluid. Moreover, such an implant can be brought in a simple manner from the normal position into the insertion position, e.g. by compression, and can thus be inserted into the body of a human or an animal in a minimally invasive manner and be used as a bone replacement implant or an intervertebral implant.

It is advantageous if the average volume of one of the plurality of cavities in fluidic connection with one another in the normal position amounts at maximum to about $1/50$ of the maximum total volume encompassed by the implant in the normal position. In this way it is assured that an adequate inherent stability of the implant can be guaranteed. In other words, this also means that at least about fifty cavities of the same or similar size are in fluidic connection with one another and form an internal structure of the implant.

The dimensional stability of the implant is increased still further if the average volume of one of the plurality of cavities in fluidic connection with one another in the normal position amounts at maximum to about $1/500$ of the maximum total volume of the implant in the normal position. The cavities in fluidic connection with one another form a cell-like structure, which becomes more stable as the number of cells per unit volume increases. In the present case this means that at least about 500 cavities of the same or similar size stand in fluidic connection with one another. In the case of implants, which have a total volume in the normal position of about 2 to 3 $cm^3$ overall, 2000 to 3000 cavities can then be configured in particular with a cavity volume of approximately 1 $mm^3$.

It would be conceivable in principle to leave the implant unchanged after insertion into the human or animal body. However, to increase the stability of the implant, and in particular permanently assure a distance between two adjacent vertebral bodies in a desired manner in the case of use as an intervertebral implant, it is favourable if the plurality of cavities in fluidic connection with one another can be filled with a fluid, preferably bone cement, after insertion of the implant between the two adjacent vertebral bodies or after insertion into the bone cavity. This configuration allows all cavities of the implant to be filled with bone cement, for example. Moreover, by virtue of the provided fluidic connection it is sufficient to inject the fluid at one location of the implant. The generally liquid bone cement upon injection can then flow into all cavities.

The implant becomes particularly stable if the plurality of cavities in fluidic connection with one another in the normal position is essentially spherical and/or honeycombed. Then, particularly when filling with bone cement, optimum pressure and stability conditions results both during injection and after curing of the bone cement.

It would be conceivable in principle to expand the implant by extraneous action after bringing it into the insertion position, in particular to bring it into its normal position again. However, it is particularly advantageous if the implant is a self-expandable implant, which, starting from the insertion position, automatically goes into the normal position without the action of external forces. The insertion of the implant into the human or animal body is thus substantially simplified. For example, the implant can be configured such that it maintains its insertion position for a certain time, in particular when there is no action from external forces, and only goes into the normal position again later. This would be achievable in particular with certain implant materials by cooling the implant in the insertion position to below a specific temperature, e.g. deep frozen. After the implant has warmed up it can then automatically go into the normal position again.

A particularly simple structure of the implant results if it is a sponge or has an essentially sponge-like structure. Such an implant can be easily brought into the insertion position, in particular compressed, and has a plurality of cavities in fluidic connection with one another.

To facilitate the automatic return of the implant from the insertion position into the normal position, it is advantageous if the implant is elastic. Energy applied to move the implant from the normal position into the insertion position can thus be stored in the implant itself and allows the automatic return from the insertion position into the normal position.

It would be conceivable in principle for the implant to be made from a biocompatible metal. However, this would have the disadvantage that it would have to constantly remain in the body. Therefore, it is favourable if the implant is made from a bioresorbable material. This enables, for example, bone to grow into the implant, namely at the locations, at which the original implant structure breaks down over time. Particularly in the case of implants filled with bone cement after insertion, this enables bone substance to grow around the cavities of the implant filled with bone cement after absorption of the implant structure and allows the strength of the inserted implant to be increased.

It is favourable if the bioresorbable material is collagen, gelatine, a polymer nonwoven, a polymer foam, hyaluronic acid, a hyaluronic acid derivative or any desired mixture of two or more of the aforementioned materials. The named materials are particularly well suited to giving the implant the required stability directly after insertion, but are also absorbable by the body in the desired way.

In some cases it is not desirable, for example, for bone cement inserted into the implant to come into contact with body tissue. Therefore it is favourable if an outer surface of the implant is provided at least partially with a fluid-tight layer.

This enables a fluid to be inserted into the implant, e.g. during the injection of liquid bone cement, without being able to come into contact with body tissue.

An optimum sealing of the implant from the natural body tissue is achieved if the entire outer surface of the implant is provided with the fluid-tight layer and if the fluid-tight layer encompasses essentially the maximum total volume in the normal position. This enables fluid inserted into the implant at one location from exiting again at another location of the implant and being able to come into contact with the natural body tissue. For example, the fluid-tight layer could be semi-permeable, so that a moisture content inside the implant can change during the course of time. This would allow the implant to be filled with a permanently elastic filler material, for example, and thus allow formation of an artificial intervertebral disc that resembles as closely as possible a natural disc.

The implant is particularly simple to produce if the fluid-tight layer is made from polylactide (PLA).

According to a preferred embodiment of the invention, it can be provided that the implant can be implanted in the insertion position in a minimally invasive manner. This configuration allows the implant to be brought to a desired location in the body through a very small surgical access point in a particularly sparing manner.

It is particularly advantageous if the insertion volume amounts at maximum to 20 per cent of the maximum total volume. This allows a surgical access point to be reduced in size by up to 80 per cent compared with conventional non-compressible implants. This causes substantially less strain on a patient and reduces the healing period for a surgical wound required for access to the surgical site.

The following description of a preferred embodiment of the invention serves for more detailed explanation in association with the drawing.

DETAILED DESCRIPTION OF THE INVENTION

Figure 1:
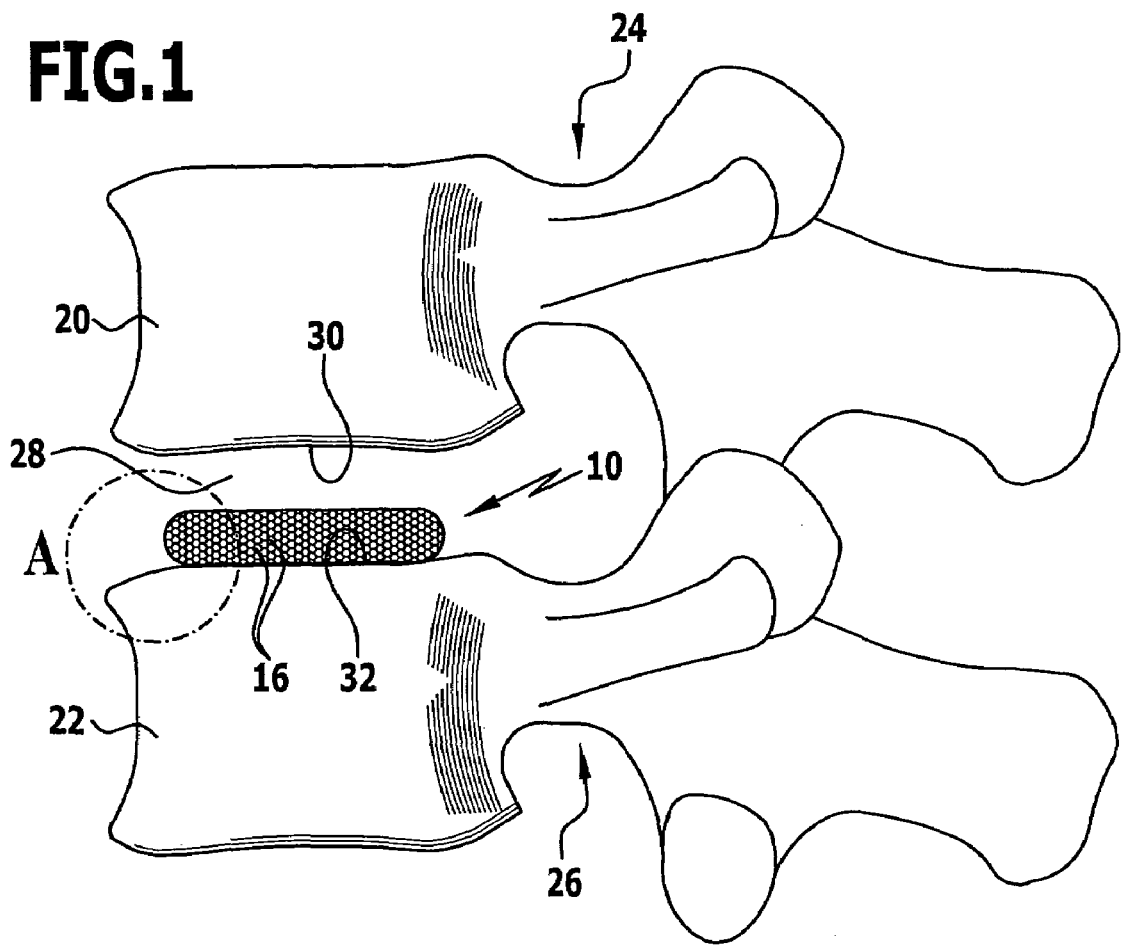
FIG. 1 is a sectional side view of a spinal column with inserted intervertebral implant in the insertion position.
Figure 1A:
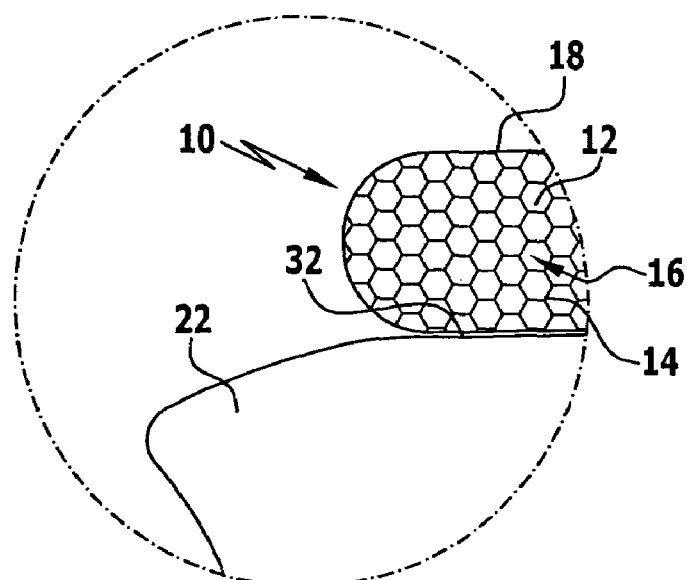
FIG. 1a is an enlarged view of section A in FIG. 1.
Figure 2:
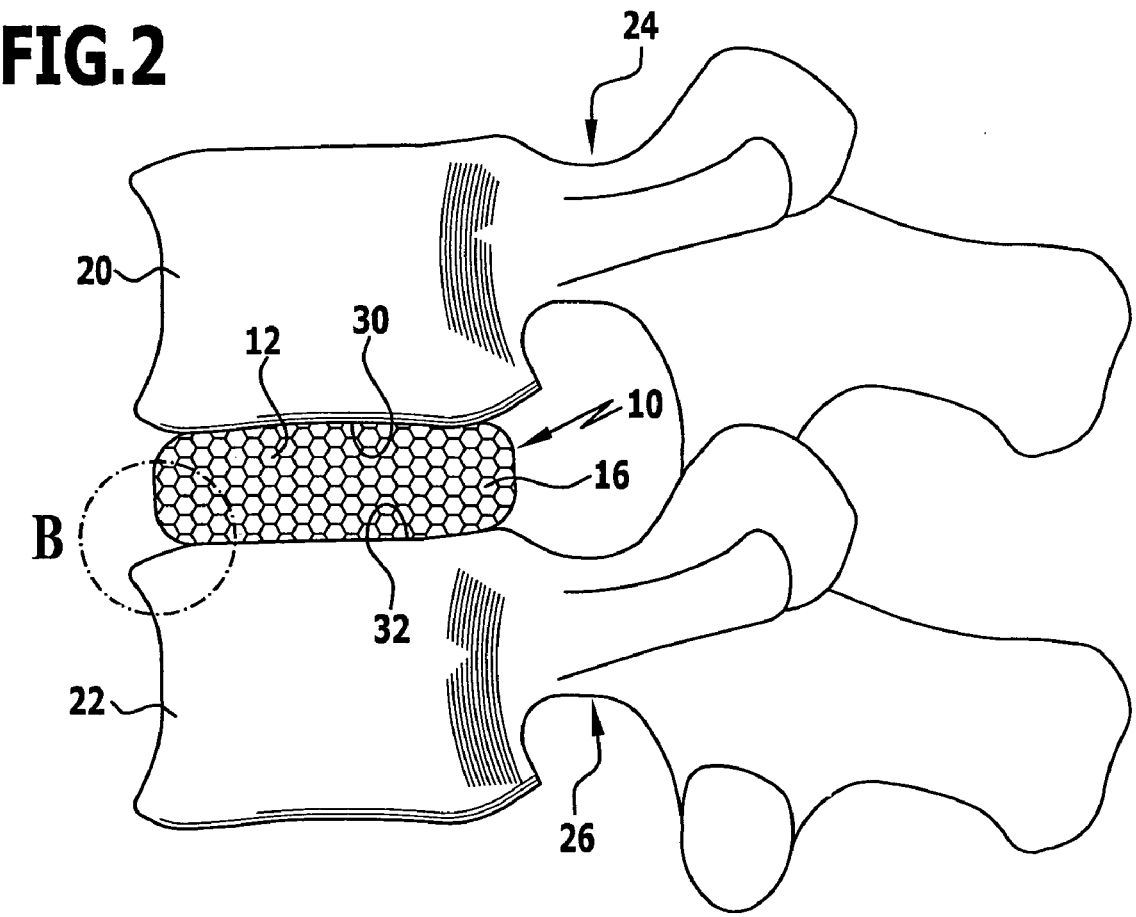
FIG. 2 is a view similar to FIG. 1, but with the intervertebral implant in the normal position.
Figure 2A:
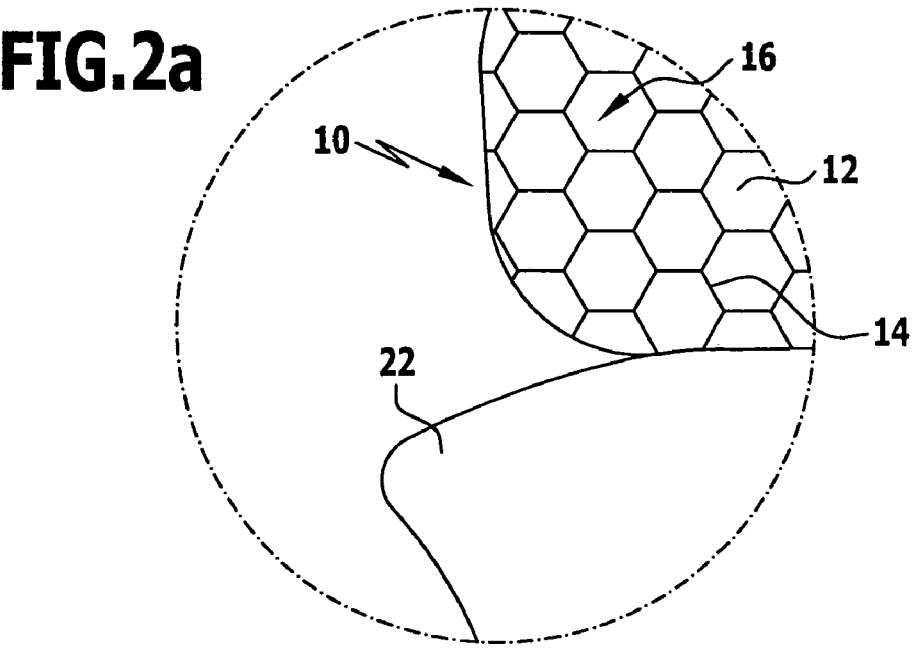
FIG. 2a is an enlarged view of section B in FIG. 2.
Figure 2B:
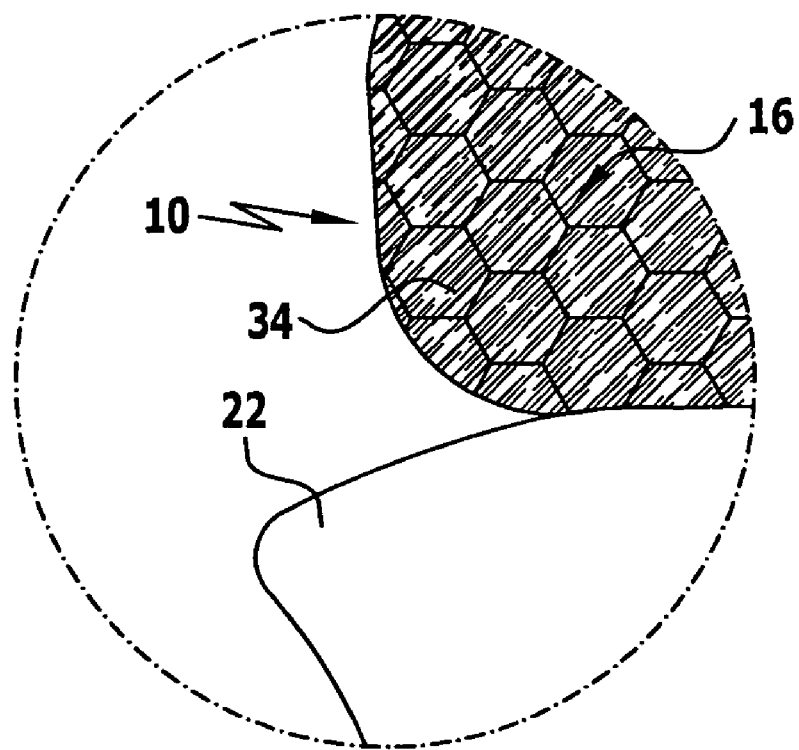
FIG. 2b is a view similar to FIG. 2, but with filled implant chambers.

FIGS. 1 and 2 show an implant according to the invention, given the overall reference 10, in the form of an intervertebral implant for replacement of a completely removed natural intervertebral disc. The implant 10 has a sponge-like structure, i.e. it comprises a plurality of cavities 12, which are enclosed by chamber walls 14 and thus form a plurality of implant chambers 16, as is clearly evident in FIG. 1a. The implant chambers 16 are each in fluidic connection with implant chambers 16 adjacent to them. An outer surface of the implant 10 is covered with a film 18 of polylactide, which thus forms a sheath for the implant as a whole.

Figure 2C:
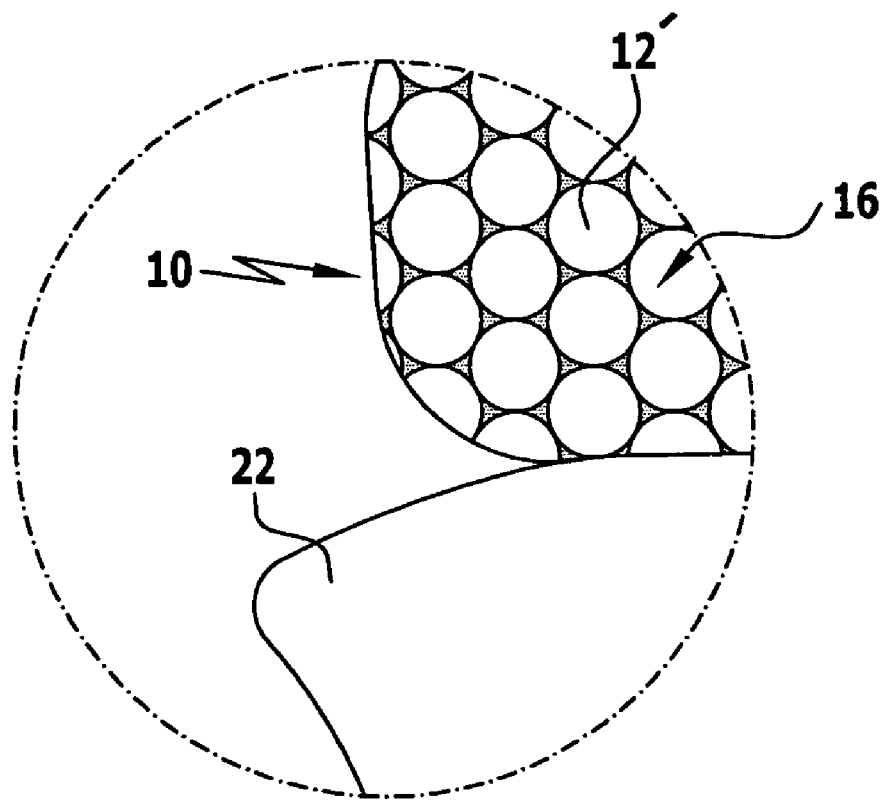
FIG. 2c is a view similar to section B of FIG. 2 of an embodiment with essentially spherical cavities.

The implant 10 is elastic overall, in particular the chamber walls 14 are formed from a bioresorbable material, e.g. collagen, gelatine, a polymer nonwoven, a polymer foam, hyaluronic acid, a hyaluronic acid derivative or a mixture of two or more of the named materials. The cavities 12 are shown with a honeycombed form in the FIGS. 1a, 2, 2a, and 2b. Irregularly shaped cavities or essentially spherical cavities (e.g., spherical cavities 12' as shown in FIG. 2c) would also be conceivable. A honeycombed structure has a particularly high stability compared with other possible forms.

Starting from a normal position, as shown in FIG. 2, in which the implant 10 encompasses a maximum total volume, the implant 10 can be brought into an insertion position, in which the implant encompasses an insertion volume, which is smaller than the maximum total volume. An example of such an insertion position is shown in FIG. 1. In this case, the overall three-dimensionally configured implant assumes an insertion volume, which only amounts to about 20 per cent of the maximum total volume.

The number of implant chambers 16 can vary. In the implant shown in the figures about 700 to 800 implant chambers are provided. In other implants about 1000 implant chambers per $cm^3$ implant volume can be provided. This means that a cavity would have about an average volume of 1 $mm^3$. In the case of usual implant volumes in the normal position of 2 to 3 $cm^3$, the implant 10 then encompasses about 2000 to 3000 implant chambers.

It will be explained briefly below how the implant 10 is used as an intervertebral implant between two adjacent vertebral bodies 20 and 22 of two vertebrae 24 and 26 of a human or animal spine.

Firstly, it is necessary to provide a surgical access point, preferably a minimally invasive surgical access point.

In a second step, the degenerated or damaged natural intervertebral disc is removed completely or partially from an intervertebral space 28 arranged between the vertebral bodies 20 and 22. In this case, the two vertebral bodies 20 and 22 can be held apart at their original distance, e.g. by means of a distraction instrument (not shown).

After removal of the intervertebral disc the implant 10 can be inserted into the intervertebral space 28. For this, it is firstly compressed, i.e. brought from the normal position shown in FIG. 2 into the insertion position shown in FIG. 1, e.g. by compression. The insertion position can be selectively "frozen", e.g. by dipping the implant 10 into liquid nitrogen.

In a subsequent step, the implant 10 assuming the insertion position is inserted into the body through the minimally invasive access point and inserted between the two vertebral bodies 20 and 22 into the intervertebral space 28. As a result of the elastic configuration of the implant 10, it then returns automatically from the insertion position into the normal position shown in FIG. 2, so that it completely fills the intervertebral space 28 and sits snugly over the whole surface of articular faces 30 and 32 of the vertebral bodies 20 and 22 pointing towards one another.

Optionally, in a further step bone cement 34 can now be injected into the cavities 12, e.g. by means of a cannula inserted into the implant 10. Because of the cavities 12 in fluidic connection with one another it is sufficient to only pierce the sheath layer at one location for filling the implant 10. However, bone cement 34 can also be injected at various locations of the implant 10. The bone cement 34 that is liquid upon injection is evenly distributed in the cavities 12 of the implant 10, since these are in fluidic connection with one another.

After the optionally injected bone cement has cured, the implant 10 maintains the normal position shown in FIG. 2. Any distraction instrument possibly used can now be removed and the minimally invasive access point closed again.

Over time the implant 10 made from a bioresorbable material is resorbed, and bone substance can penetrate the bone cement structure in place of the then absorbed chamber walls 14 and guarantee a permanent fusion of the two adjacent vertebral bodies 20 and 22.

The invention claimed is:

1. Implant for insertion into a bone cavity or between two adjacent vertebral bodies of a human or animal spine, said implant comprising:
    a fluid-tight outer layer;
    a plurality of interconnected cavities within the fluid-tight outer layer, the plurality of interconnected cavities having a sponge-like structure and being in fluidic connection with one another and designed to be brought from a normal position into an insertion position,
    wherein:
        in said normal position the implant encompasses a maximum total volume and in said insertion position the implant encompasses an insertion volume, which is smaller than the maximum total volume,
        a net volume encompassed in the normal position by the plurality of cavities in fluidic connection with one another is smaller than the maximum total volume;
        the implant is a self-expandable implant, which, starting from the insertion position, automatically expands into the normal position; and
        the implant is made from a bioresorbable material.

2. Implant according to claim 1, wherein an average volume of one of the plurality of cavities in fluidic connection with one another in the normal position amounts at maximum to about 1/50 of the maximum total volume encompassed by the implant in the normal position.

3. Implant according to claim 2, wherein the plurality of cavities in fluidic connection with one another in the normal position are at least one of essentially spherical and honeycombed.

4. Implant according to claim 1, wherein an average volume of one of the plurality of cavities in fluidic connection with one another in the normal position amounts at maximum to about 1/500 of the maximum total volume encompassed by the implant in the normal position.

5. Implant according to claim 1, wherein
    the plurality of cavities in fluidic connection with one another are designed to be filled with a fluid after insertion of the implant between the two adjacent vertebral bodies or into the bone cavity and expansion of said implant into said normal state.

6. Implant according to claim 5, wherein the implant is adapted such that the insertion volume amounts at maximum to 20% of the maximum total volume.

7. Implant according to claim 5, wherein the bioresorbable material comprises at least one of collagen, gelatine, a polymer nonwoven, a polymer foam, hyaluronic acid, or a hyaluronic acid derivative.

8. Implant according to claim 1, wherein the plurality of cavities in fluidic connection with one another in the normal position are at least one of essentially spherical and honeycombed.

9. Implant according to claim 1, wherein the implant is elastic.

10. Implant according to claim 1, wherein the bioresorbable material comprises at least one of collagen, gelatine, a polymer nonwoven, a polymer foam, hyaluronic acid, or a hyaluronic acid derivative.

11. Implant according to claim 1, wherein the fluid-tight outer layer completely surrounds the inner cavities.

12. Implant according to claim 11, wherein the fluid-tight layer is made from polylactide (PLA).

13. Implant according to claim 1, wherein the fluid-tight outer layer encompasses essentially the maximum total volume in the normal position.

14. Implant according to claim 1, wherein the implant is designed to be implanted in the insertion position in a minimally invasive manner.

15. Implant according to claim 1, wherein the implant is adapted such that the insertion volume amounts at maximum to 20% of the maximum total volume.

16. A method for inserting an implant into a bone cavity or between two adjacent vertebral bodies of a human or animal spine, comprising:
    providing a self-expandable bioresorbable implant, said implant comprising a fluid-tight outer layer and a plurality of interconnected cavities within the fluid-tight outer layer, the plurality of interconnected cavities having a sponge-like structure and being in fluidic connection with one another, with said cavities in an unfilled state;
    compressing the implant from a normal position in which the implant encompasses a maximum total volume into an insertion position in which the implant encompasses an insertion volume, which is smaller than the maximum total volume;
    inserting the compressed implant into one of said bone cavity or between said two adjacent vertebral bodies;
    allowing the compressed implant to automatically expand into the normal position, with said cavities remaining in said unfilled state; and
    injecting a fluid into said implant after said expansion into said normal position;
    wherein a net volume encompassed in the normal position by the plurality of cavities in fluidic connection with one another is smaller than the maximum total volume.

17. A method in accordance with claim 16, wherein the fluid comprises bone cement.

18. A method in accordance with claim 16, further comprising:
    freezing said implant in said compressed state prior to said inserting step.

* * * * *